US006685658B1

(12) United States Patent
Dietz et al.

(10) Patent No.: US 6,685,658 B1
(45) Date of Patent: Feb. 3, 2004

(54) DEVICE AND METHOD FOR A LOCOMOTION THERAPY

(75) Inventors: Volker Dietz, Küsnacht (CH); Gery Colombo, Zürich (DE); Rüdiger Rupp, Hockenheim (DE)

(73) Assignee: Balgrist/Schweiz. Paraplegikerzentrum, Zurich (CH)

(*) Notice: Subject to any disclaimer, the term of this patent is extended or adjusted under 35 U.S.C. 154(b) by 0 days.

(21) Appl. No.: 09/958,034

(22) PCT Filed: Apr. 7, 2000

(86) PCT No.: PCT/CH00/00203

§ 371 (c)(1),
(2), (4) Date: Dec. 3, 2001

(87) PCT Pub. No.: WO00/61059

PCT Pub. Date: Oct. 19, 2000

(30) Foreign Application Priority Data

Apr. 7, 1999 (CH) .............................................. 647/99

(51) Int. Cl.[7] ........................... A61H 1/02; A61F 5/042

(52) U.S. Cl. .............................. 601/5; 601/26; 601/35; 606/242; 606/244; 128/845

(58) Field of Search .............................. 601/31–36, 23, 601/24, 29, 5; 606/240, 242–5, 237; 128/845; 482/79, 80

(56) References Cited

U.S. PATENT DOCUMENTS 2,695,017 A * 11/1954 Herrmeyer .................. 606/245
4,986,261 A 1/1991 Iams et al.
5,063,918 A * 11/1991 Guhl .......................... 606/242
5,239,987 A 8/1993 Kaiser et al.
5,333,604 A * 8/1994 Green et al. .................. 601/33
5,782,869 A * 7/1998 Berdut ....................... 606/242
5,800,366 A * 9/1998 Bertrand ...................... 601/24
5,901,581 A * 5/1999 Chen et al. ................... 601/34

FOREIGN PATENT DOCUMENTS

EP 0 121 642 A2 10/1984
GB 983743 2/1965

OTHER PUBLICATIONS

I. Wickelgren, "Teaching the Spinal Cord to Walk", Science, vol. 279, Jan. 16, 1998, pp. 319–321.

* cited by examiner

*Primary Examiner*—Danton D. DeMille
(74) *Attorney, Agent, or Firm*—Burns, Doane, Swecker & Mathis, L.L.P.

(57) ABSTRACT

The invention relates to an apparatus which actively moves the legs of a disabled person in a movement pattern that is similar to physiological walking. The inclination of the standing table can be adjusted between a horizontal and a vertical position as desired. The patient is fixed to the standing table by means of a belt gear. The aim of this kind of rehabilitating locomotion therapy is to activate the locomotion structures in the spinal cord in order to improve the muscular situation in a time optimal manner, to prevent the intensity of spasticity and to improve the circulatory conditions.

12 Claims, 7 Drawing Sheets

Fig. 2
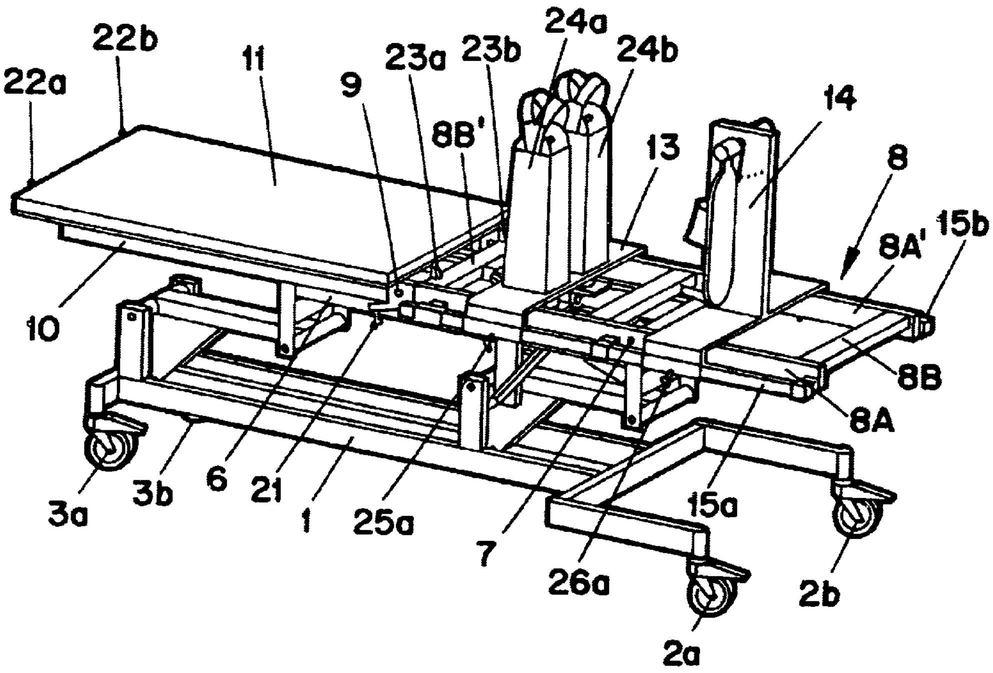
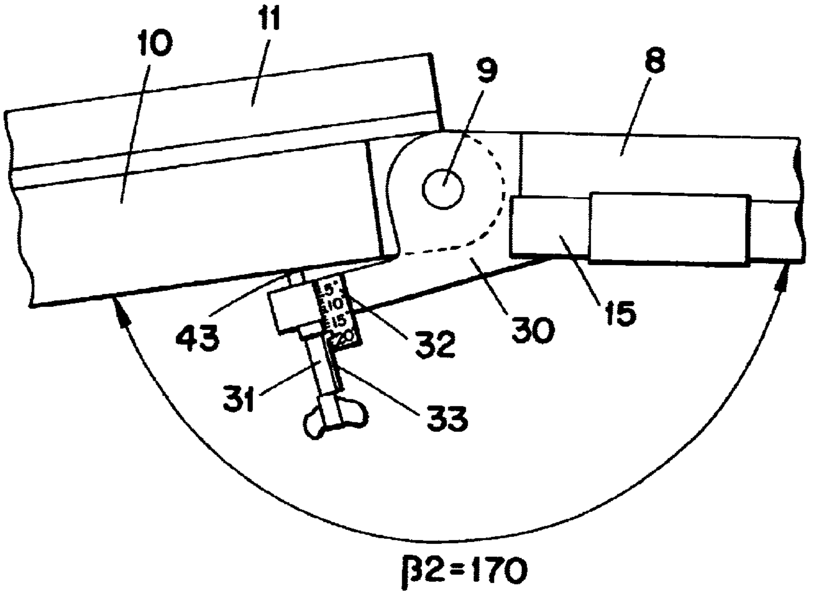
Fig. 3

Fig. 4A
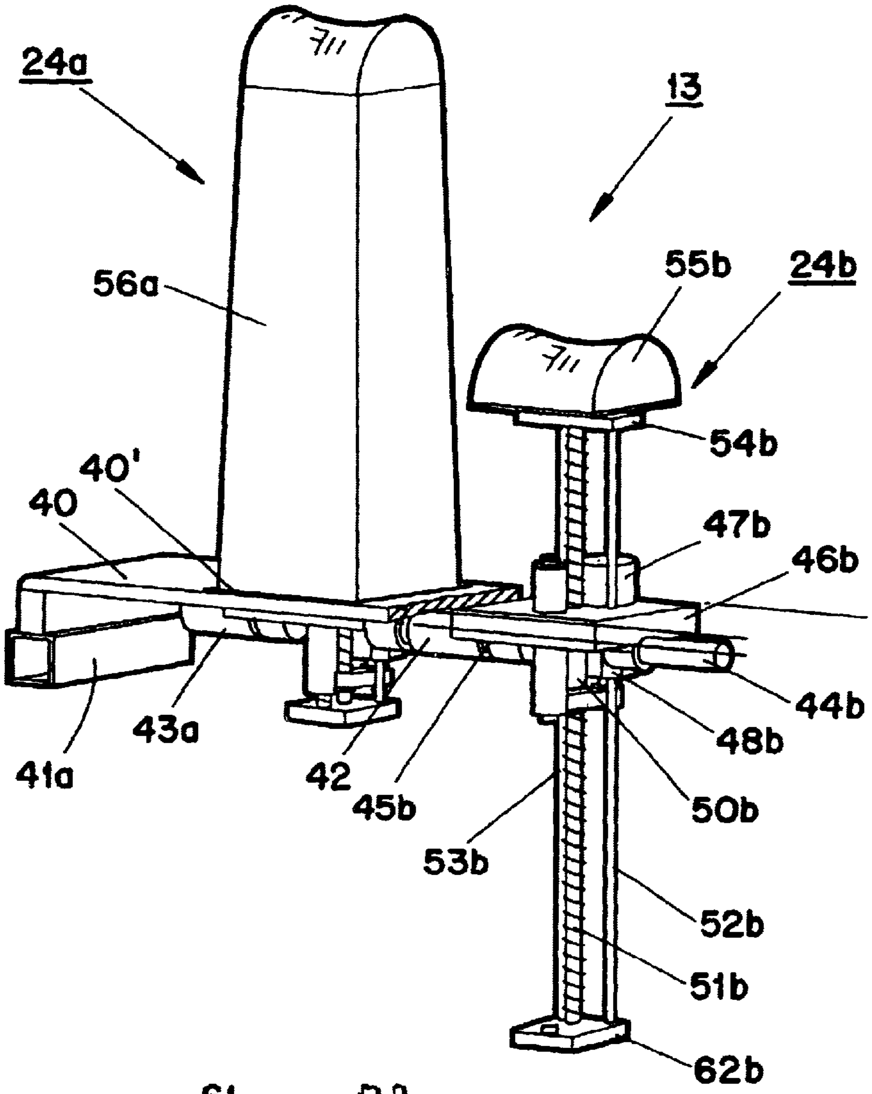
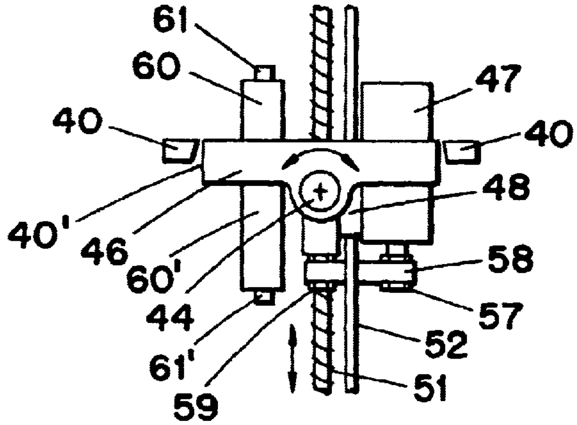
Fig. 4B

Fig. 8A
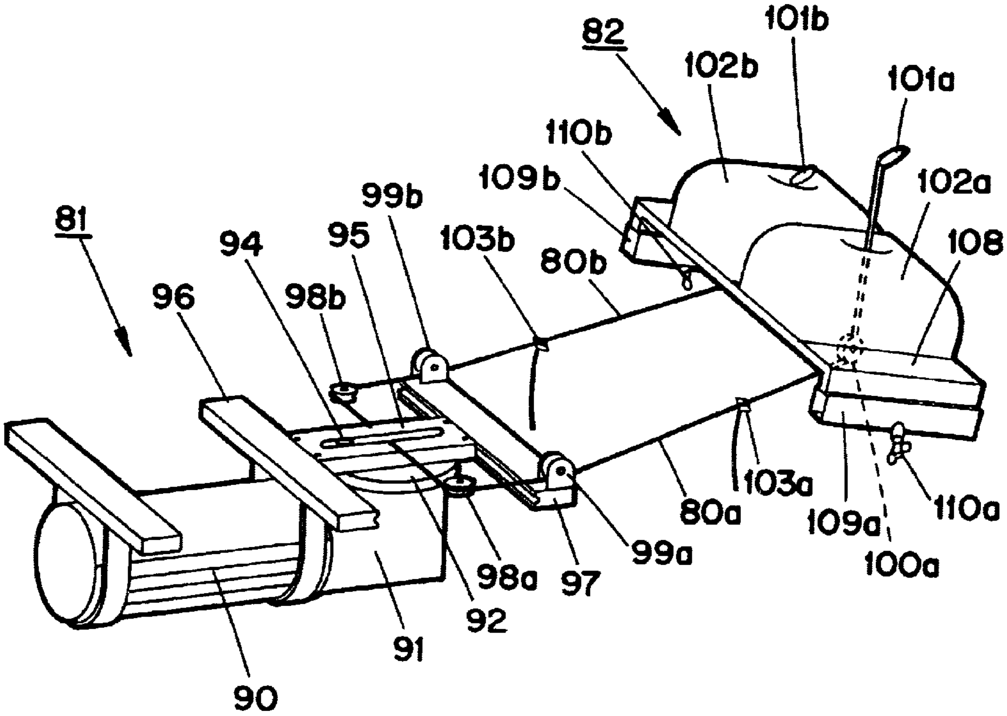
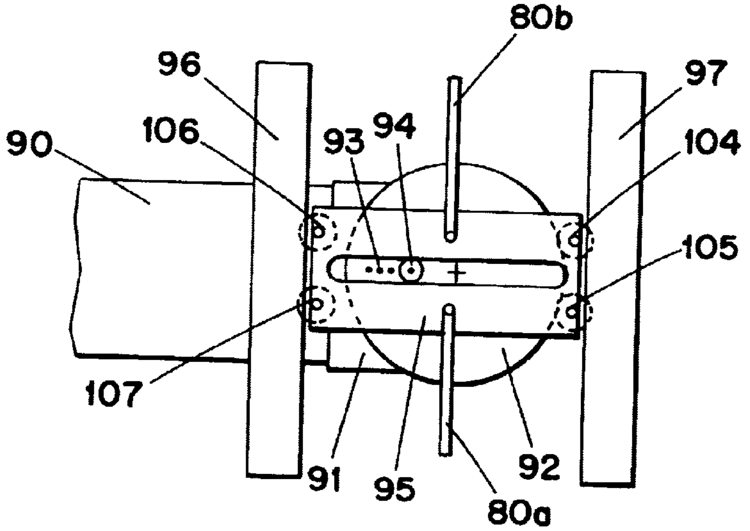
Fig. 8B

DEVICE AND METHOD FOR A LOCOMOTION THERAPY

FIELD OF THE INVENTION

The invention relates to an apparatus and a process in order to begin a locomotion training of patients with walking impediments in an early phase of rehabilitation.

BACKGROUND OF THE INVENTION

In incompletely paraplegic patients the possibility has been shown to exist of improving walking ability up to normality by means of an adequate locomotion training. The required therapy at present takes place on a moving belt, where walking is first made possible for the patient by defined weight relief and partially by additional assisting guidance of the legs by physiotherapists (Wickelgren, I. Teaching the spinal cord to walk. Science, 1998, 279, 319–321). This kind of locomotion therapy can of course only be started when there is sufficient stability of the circulation, since the patient has to remain for a long time in an upright position. The required circulatory stability is as a rule not present in the first weeks after the onset of the spinal cord lesion.

In the rehabilitation of patients with limited motion of the legs or after orthopedic operations, various driven ortheses are already in use which actively move the legs of recumbent patients.

U.S. Pat. No. 5,239,987 (1993) describes such a system. In this apparatus, the legs are guided primarily in that the lower leg is moved relative to the thigh. However, no apparatus exists in which a knee extension with weight loading on the sole of the foot is attained in the extended phase ("standing phase") of the movement cycle. Hip joint extension is also not present in the said mechanisms.

U.S. Pat. No. 4,986,261 (1991) describes an apparatus which also effects a hip joint extension. However, the knee joint is not moved there as in physiological walking.

None of the described systems make it possible to move the legs while the inclination of the patient can be simultaneously adjusted.

SUMMARY OF THE INVENTION

The present invention has as its object to make possible an intensive walking training (activation of the motion centers in the spinal cord) of paraparetic and hemiparetic patients, before they are physically able to take part in a moving belt training, that is, in a still unstable circulatory situation. The possibility is to be provided of steadily bringing the patient's body closer to the vertical position. The aim of the apparatus according to the invention is to provide a so-called "active standing table" (tilting table) which makes possible the movement of the legs of paraplegic patients in a manner physiologically similar to walking, without the necessity of having them stand upright.

This object is attained according to the invention with an active standing table according to the wording of patent claim 1, and an associated process for the operation of the active standing table according to the wording of patent claim 8.

BRIEF DESCRIPTION OF THE DRAWINGS

The invention is described in detail hereinafter using the accompanying drawings.

FIG. 2 shows an overall view of a first embodiment example of an active standing table in a horizontal position, FIG. 3 shows a mechanism for the setting of the hip extension angle, FIG. 4A shows the knee mechanism of FIG. 2, in a perspective diagram, FIG. 4B shows the knee mechanism of FIG. 2, in a side view, FIG. 8A shows the knee mechanism of FIG. 7, in a perspective diagram, FIG. 8B shows a top view of the eccentric drive of FIG. 7.

DETAILED DESCRIPTION OF THE INVENTION

Figure 1:
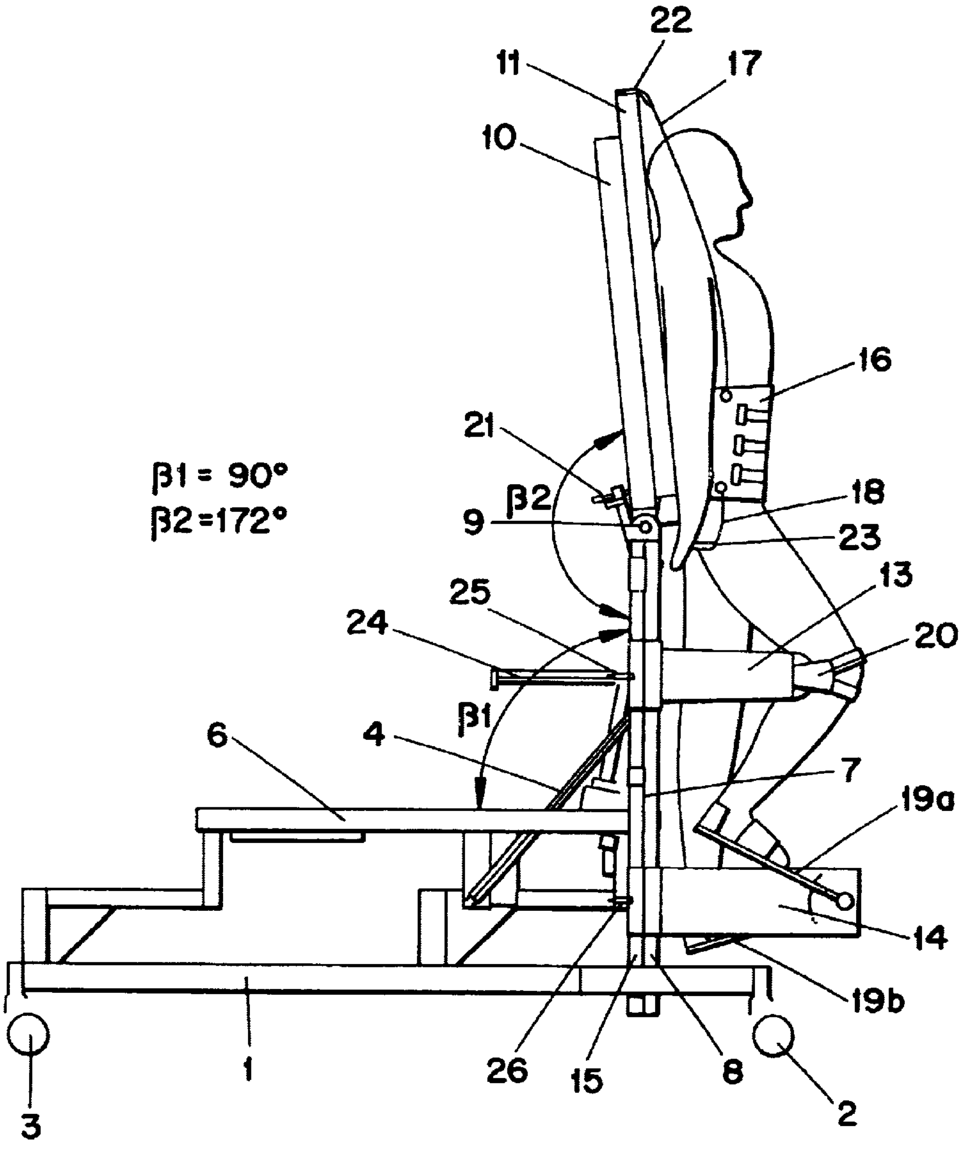
FIG. 1 shows a side view of an active standing table with a patient in a vertical position.

FIG. 1 shows a side view of the active standing table with a patient in a vertical position. A main support serves as a base, as is known for conventional standing tables. It consists of a chassis 1 with rollers 2 and 3 and a height-adjustable frame 6 (e.g., "Super Tilt Table", Gymna Co., Belgium). The frame 6 can be height-adjusted manually or with a drive (not shown). A joint 7 is mounted on the frame 6 and articulates to the frame 6 a leg portion 8 consisting of two beams and two cross-struts (see FIG. 2). The leg portion 8 is further connected by means of a joint 9 to a head portion 10 (frame similar to that of the leg portion 8), on which a support surface 11 is situated, consisting of a wooden board with a foam lining. So that the angle of the standing table can be continuously increased toward the vertical during a therapy with the active standing table, the leg portion 8 can be rotated around the joint 7 by a drive 4 and can thus be set at an angle of inclination β1 in order to be able to carry out a treatment in a known manner at different angles of inclination. The angle of inclination β1 in the Figure is 90°, which corresponds to a vertical position of the patient. By means of the adjustability of the angle of inclination, patients with unstable blood circulation can be treated already in the recumbent position, and then continuously brought into the vertical position during the therapy, according to their status, the angle of inclination β1 being gently increased.

It is possible to fix an inclination between the leg portion 8 and the head portion 10 with a mechanism 21 for setting the hip extension, a hip extension angle β2 being thereby defined. A hip extension of the legs can thus be realized during the therapy. When the standing table is situated in a horizontal position, β2 is always 180°, since the head portion 10 abuts on the frame 6. If now the angle β1 is increased, β2 also is decreased, until the mechanism 21 comes up against its stop and the head portion is likewise brought upward. In this Figure, the angle β2 is 172°, giving a hip extension value for the patient of 8°; preferred values are about 12°.

On the leg portion 8 there are a knee mechanism 13, with two knee drives 24, and a foot mechanism 14. These two mechanisms can be displaced parallel to the leg portion, on two rails 15 which are fastened one on each side of the leg portion 8, thus permitting the standing table to be suited to the anatomy of different patients.

In order to carry out a therapy, the support surface 11 is tilted into the horizontal position and brought, by means of the height adjustment of the main support, to the same height as the hospital bed on which the patient is lying. The patient is then transferred to the support surface 11, so that his upper body comes to lie on the support surface, and his hip joints on the lower edge of the support surface. A locating belt 16 is then placed around the patient's hips, and is fastened with fastening bands 17 to eyelets 22 at the upper side of the support surface 11 and with fastening bands 18 to eyelets 23 at the lower side of the support surface. This fastening prevents an up and down movement of the upper body during the therapy. It is provided so as to minimize movements of the trunk, in order to prevent injuries to the possibly still unstable spine. The locating belt 16 corresponds to a belt such as is used in a standard manner for relieving weight in moving belt training of paraplegics (e.g., moving-belt belt article "Walker", Hamster's Parachute Service Co., Austria).

When the patient is fastened to the support surface, the knee mechanism 13 is displaced on the rails 15 such that the knee drive 24 comes to lie directly under the hollows of the patient's knees. The knee mechanism is fixed there with securing screws 25. The foot mechanism 14 is then also displaced, so that an extension (stretching) of the patient's legs presses footplates 19*a* and 19*b* down as far as a stop (see FIG. 5). The foot mechanism 14 is fixed in the correct position with securing screws 26. Marks present on the rails 15 permit the position of the foot mechanism 13 and knee mechanism 14 to be read off. Using the marks, the settings can easily be reproduced in repeated therapies.

Figure 6:
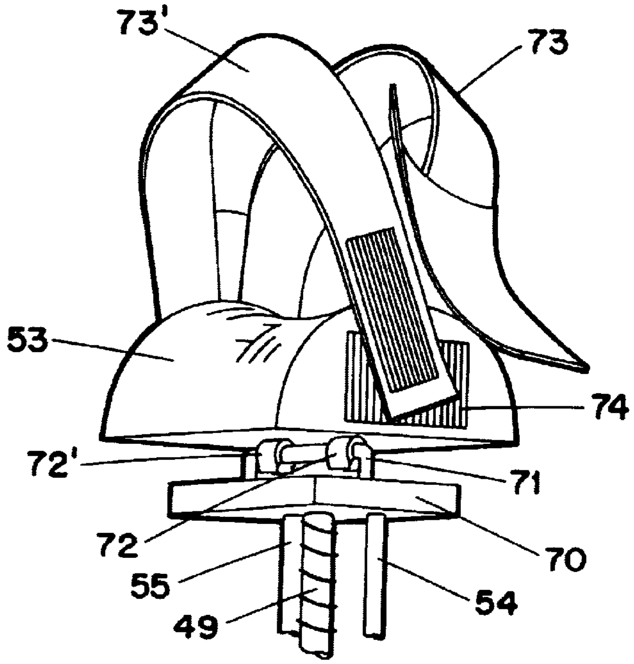
FIG. 6 shows a knee cuff of FIG. 2, in a perspective diagram.

Knee cuffs 20 are then fastened around the patient's knees (see FIG. 6). These cuffs are fastened to the knee drives 24, which thus pull the patient's knee down or push it up, during the therapy. This respectively effects a stretching or a bending of the legs. In the Figure, the patient's right leg is shown in the bent state and the left leg in the stretched state. It is to be mentioned that at the beginning of the therapy the two knee drives 24 are retract-ed. The patient can thus be easily transferred to the standing table. A knee drive is first extended when the treatment begins, thus bending a leg.

During the locomotion therapy, the knee drives 24 are alternately moved upward and downward, so that the legs of the patient move in a path of motion which is similar to that in normal walking. Thus the sensory input (afferent) from the legs provides information for the spinal locomotion centers in the spinal cord which is similar to that in physiological walking, and excites the locomotion centers to an activation.

FIG. 2 shows an overall view of a first embodiment example of an active standing table in a horizontal position. The main support, consisting of a chassis 1 with rollers 2*a*, 2*b*, 3*a* and 3*b*, and the height-adjustable frame 6, can again be seen. The leg portion 8, a frame consisting of two beams 8A and 8A and also two cross struts 8B and 8B', is connected to the frame 6 by means of the joint 7. The leg portion 8 is further connected by means of the joint 9 to the head portion 10, on which the support surface 11 is situated. The mechanism 21 for setting the hip extension is situated with the joint 9.

The knee mechanism 13 with the two knee drives 24*a* and 24*b*, and a foot mechanism 14, are situated on the leg portion 8, and can respectively be displaced on the rails 15*a* and 15*b* parallel to the leg portion 8. The securing screws 25 and 26 are situated on the leg portion 13 [sic] and on the foot portion 14 [sic], and serve for fastening on the rails 15*a* or 15*b*, respectively.

Eyelets 22*a*, 22*b*, 23*a* and 23*b* are installed on the support surface 11 for fixing the patient.

FIG. 3 shows a side view of the mechanism for setting the hip extension angle. The joint 9 can be seen, with a portion of each of the leg portion 8, the head portion 10, the support surface 11 and the rail 15. An elbow 30 is installed on the leg portion 8. A limiting screw 31 is situated in a screw thread in this elbow 30. If the standing table is in the horizontal position (angle of inclination $\beta 1=0$), the head portion 10 is situated on the main support of the tilting table and the angle $\beta 2$ is 180°. If now the angle of inclination is increased, the angle $\beta 2$ is decreased until the head portion 10 abuts against the screw head 43 of the limiting screw 31, and the head portion is brought upward. If now the limiting screw 31 is screwed further into the elbow 30, the angle $\beta 2$ becomes correspondingly greater; if screwed out, correspondingly smaller. A pointer 33 shows, on a scale 32, what hip extension angle for the patient is set with the limiting screw. The hip extension angle corresponds to $180°-\beta 2$.

FIG. 4A shows the knee mechanism 13 of FIG. 2, in a perspective diagram. Rectangular tubes 41*a* and 41*b* (not shown) are situated on each side of a crosspiece 40. These serve as guides for the knee mechanism 13 on the rails on the leg portion. The crosspiece 40 has two rectangular openings 40' in which the two knee drives 24*a* and 24*b* are situated. These two drives are identical in construction, only one being numbered in the Figure. Bearings 42, 43*a* and 43*b* (not shown) are mounted on the crosspiece 40 on the under side, and suspension shafts 44*b* and also 45*b* can freely rotate in them. These suspension shafts are each attached to a baseplate 46*b*. Due to this mounting, the knee drives can turn, so that they are moved around the rotation axis of the hip joint by the knee motion of the patient, during a bending or stretching. A motor 47*b* is fastened in the baseplate 46*b*, and two guide tubes (48*b* or 49*b*, not shown) are inserted. Likewise, a guide 50*b* is situated in the baseplate 46*b*, and a threaded rod 51*b* is free to turn in it. The construction of the drive by means of a threaded rod is described in detail in FIG. 4B. A respective guide rod 52*b* and 53*b* can be displaced upward and downward in the respective guide tubes 48*b*, 49*b*. If now the linear drive moves upward or downward, a plate 54*b* and a knee cushion 55*b* fastened to it are brought upward or downward. The patient's knee is caused to flex when the knee cushion moves upward, and is pulled into extension when the knee cuff (see FIG. 6) moves downward. The two guide bars 52*b* and 53*b*, which are guided in the guide tubes 48*b* and 49*b*, provide for the lateral stability of the knee drive, so that the patient's leg does not incline sideways. The guide tubes 48*b* and 49*b*, and also the threaded rod 51*b*, are mounted at the upper end in the plate 54*b* and at the lower end in a plate 62*b*.

A protective sheath 56*a* made of rubber protects the patient from injury on the knee drives.

FIG. 4B shows a side view of the knee mechanism 13 of FIG. 2. The principle of the drive is explained more accurately using this Figure. The crosspiece 40 can be seen, with the baseplate 46 let into the opening 40'. The suspension shaft 44 can be seen on the baseplate 46, and permits a rotation of the knee drive around the axis indicated by the round arrow. The guide tube 48 permits the guide bar 52 to displace the threaded rod 51 through the guide 50. The motor 47, which is fixedly mounted in the baseplate 46, drives a gearwheel 59 mounted on the guide 50 by means of a gearwheel 57 and a V-belt 58. There is a screw thread in the gearwheel 59. When now the gearwheel is driven by the motor 47, the threaded rod 51 moves upward or downward in the baseplate 46, as indicated by the straight arrow.

Respective limit switches 60 and 60' are situated above and below on the baseplate 46. These serve to indicate the attainment of an end position to a control unit which controls the movement of the drive. If the drive has reached the lowest point, the plate presses with the knee cuff on a contact button 61 and the limit switch 60 signals to the control unit that the motor has to run in the opposite direction. The drive then travels upward until the lower plate presses against a contact button 61', and the limit switch 60' sends the control unit a further signal to change over.

Figure 5:
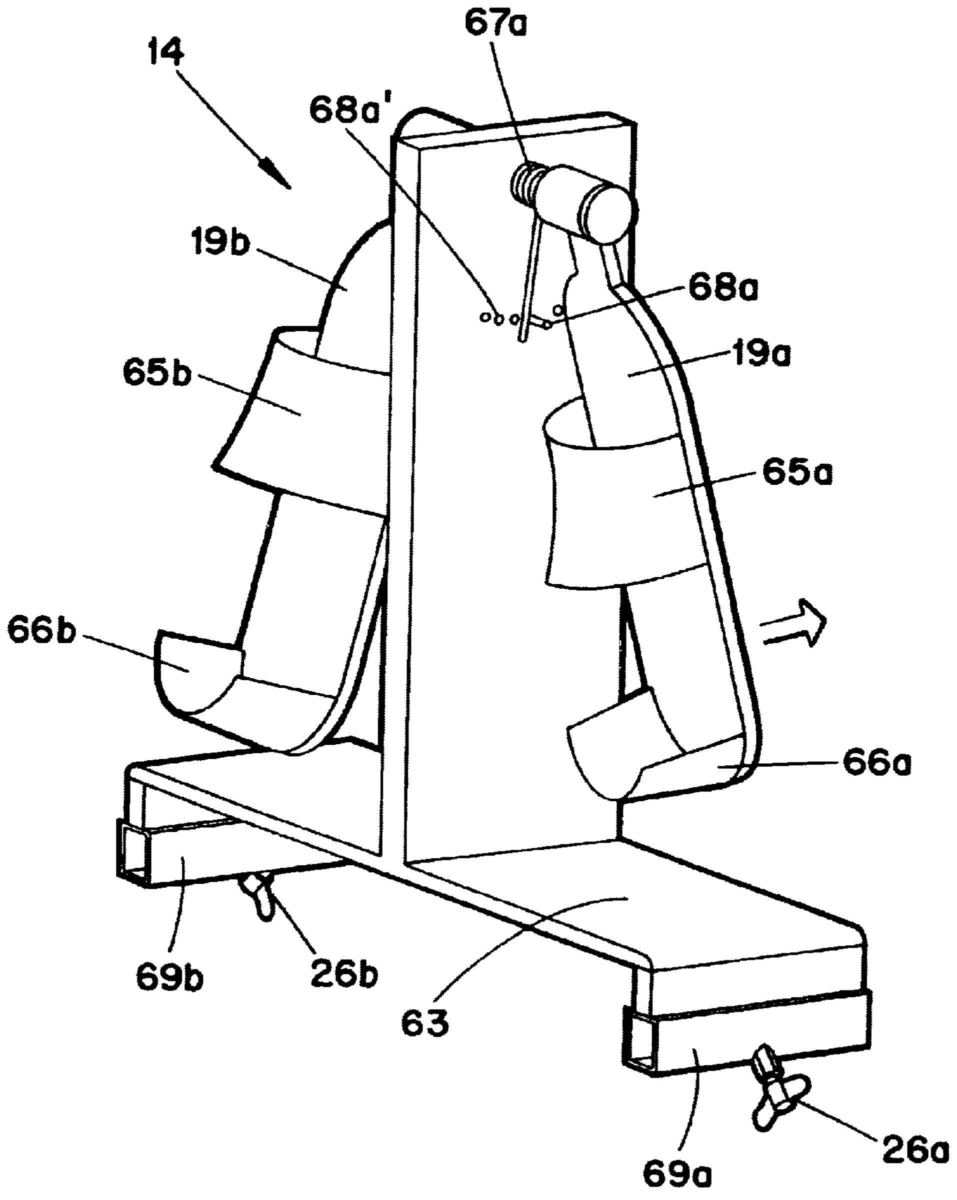
FIG. 5 shows the foot mechanism of FIG. 2, in a perspective diagram.

FIG. 5 shows the foot mechanism 14 of FIG. 2 in a perspective diagram. A respective rectangular tube 69*a*, 69*b* is fixedly connect ed to the lower side of a T-piece 63. These serve as guides for the foot mechanism on the rails fastened to the leg portion. The foot mechanism can be secured by the fixing screws 26*a* and 26*b* at the correct place during therapy. A respective footplate 19*a* and 19*b*, able to rotate around a bearing at the attachment point to the T-piece, is situated at either side at the upper end of the T-piece 63. The footplates are of identical construction, all parts appearing symmetrically on both sides. The patient's feet can be introduced into respective elastic loops 65*a* and 65*b* on the footplates. They are then protected from slipping out by the heel holders 66*a* and 66*b*.

The footplates 19*a* and 19*b* are each connected to a respective spring 67*a* or 67*b* (not shown). These are tensioned at a respective bolt 68*a* or 68*b* (not shown) when the footplate is pressed downward by the patient (in the direction of the arrow). This produces a pressure on the sole of the patient's foot in the extended phase of the movement cycle, and simulates a weight force like that experienced in walking. The strength of this weight force can be adjusted by a displacement of the bolt 68*a* into the respective holes 68*a'*. When the angle of inclination of the standing table becomes greater, normally the weight force which acts on the legs also becomes greater. This effect can be compensated and controlled in that the patient is pulled more or less upward with the fastening bands and the locating belt.

FIG. 6 shows a perspective diagram of a knee cuff of FIG. 2. A plate 70 is securely mounted on the upper ends of the threaded rod 49 and of the guide bars 54 and 55. A yoke 71 is attached to this plate, and a knee cushion 53 can be fastened to the yoke by two clip mechanisms 72 and 72'. This knee cushion 53 is of foam material covered with plastic. The clip mechanism holds the knee cushion firmly enough to effect an extension of the knee when the knee drive is pulled downward. The connection is however released when the patient's knee cannot be extended for any reason in a faulty manipulation. This serves as a load protection for the patient's legs and protects him from injury. The clip mechanism releases the knee cushion at load forces or tensile forces of 150–200 N, preferably of 180 N. A knee cuff consisting of two hook-and-loop fastener bands 73 and 73' is fastened to the knee cushion 53 and permits the patient's knee to be fastened to the knee cushion, in that the bands are mounted on the hook-and-loop strips 74. The two bands are fastened to the knee such that the patient's kneecap is situated between the bands and is not subjected to pressure by them when the leg is extended.

Figure 7:
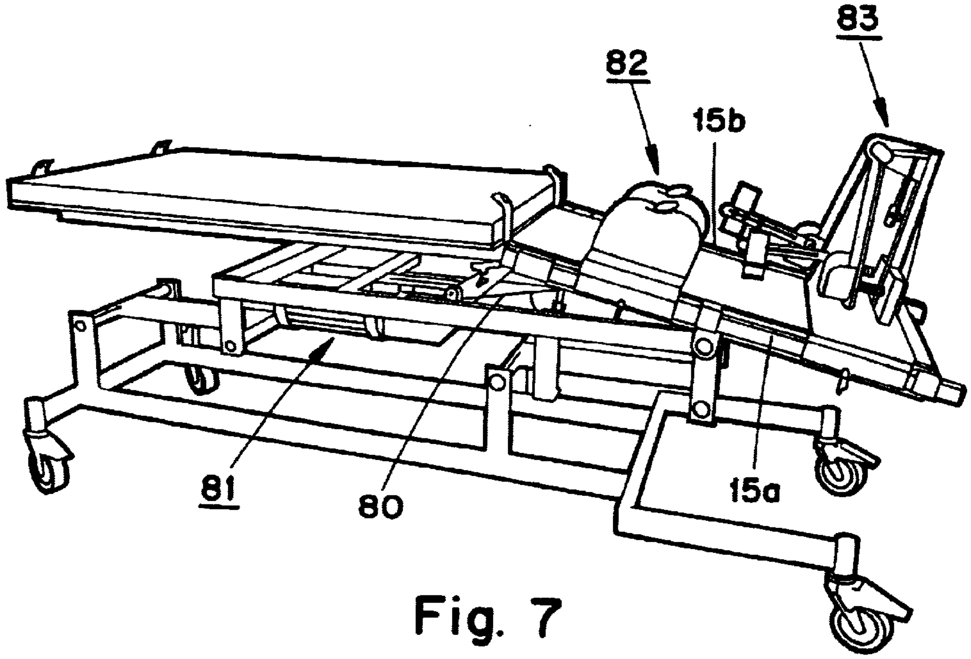
FIG. 7 shows an overall view of a second embodiment example of an active standing table in a horizontal position.

FIG. 7 shows an overall view of a second embodiment example of an active standing table in a horizontal position. The basic construction is identical to that of the first embodiment example. Differently from this, in the present training apparatus the patient's legs are driven by an eccentric drive 81, described in detail in FIG. 8, via a cable 80, and not with a linear drive. A knee portion 82 and a foot portion 83 can be displaced on the rails 15*a* and 15*b* and thus matched to the leg length of the patient.

FIG. 8 shows the knee mechanism of FIG. 7 in a perspective diagram. It consists of an eccentric drive 81, cables 80*a* and 80*b* (nylon cables), and also the knee portion 82. A gear transmission 91 is installed on a motor 90 and drives an eccentric disk 92 with a pin 94 inserted into it. When the eccentric disk 92 rotates, the pin 94 now moves on a circular path. A slide 95 in which the pin 94 is guided is moved to and fro by this circular motion, the slide being itself guided in guide rails 96 and 97. The movement of the slide 95 effects a tensile force on a respective one of the cables 80*a* or 80*b*. The cables are guided over rollers 98*a*, 98*b*, 99*a*, 99*b*, 100*a* and 100*b* (not shown), and then pull the patient's knee into an extension by means of a hook 101*a* or 101*b* on the knee cuff.

Cushions 102*a* and 102*b* of foam material covered with plastic protect the hollows of the patient's knees from injury during extension, and press the knee toward flexion again when the cable 80*a* or 80*b* is relaxed. The cushions are on a plate 108 which has guide tubes 109*a* and 109*b* on either side, with fastening screws 110*a* and 110*b*.

A respective tensioning device 103*a* or 103*b* is mounted on the cables 80*a* and 80*b*, and enables the cables to be adjusted in length. This permits the tension on the hooks 101*a* or 101*b* to be adjusted so that the patient's knee is stretched as far as an extension by the movement of the eccentric disk 92.

Hook-and-loop bands similar to those described in FIG. 6 can be used as knee cuffs with which the patient's knee is fastened to the hooks 101*a* or 101*b*.

FIG. 8B shows a top view of the eccentric drive of FIG. 7. The motor 90 can be seen, with the gear transmission 91 on which the eccentric drive 92 is situated. In this, various holes 93 are provided so that the pin 94 can be inserted into the eccentric disk 92 at different radii. The stroke length of the knee movement can be set larger or smaller by the different positioning of the pin 94 in the holes 93. Rollers 104–107 are mounted on the slide 95 and mount the plate in the guide rails 96 and 97. The two cables 80*a* and 80*b* are also fastened to the slide 95.

In contrast to the first embodiment example, a considerably simpler control mechanism is required here, since the motor can simply rotate and the extension or flexion of the leg results automatically. The control unit controls only the speed of the motor 90 and thus controls the frequency of the movement of the patient's leg. In the first embodiment example, the control unit has to always switch the drive over on reaching the end positions, from an upward movement to a downward movement and vice versa.

Figure 9:
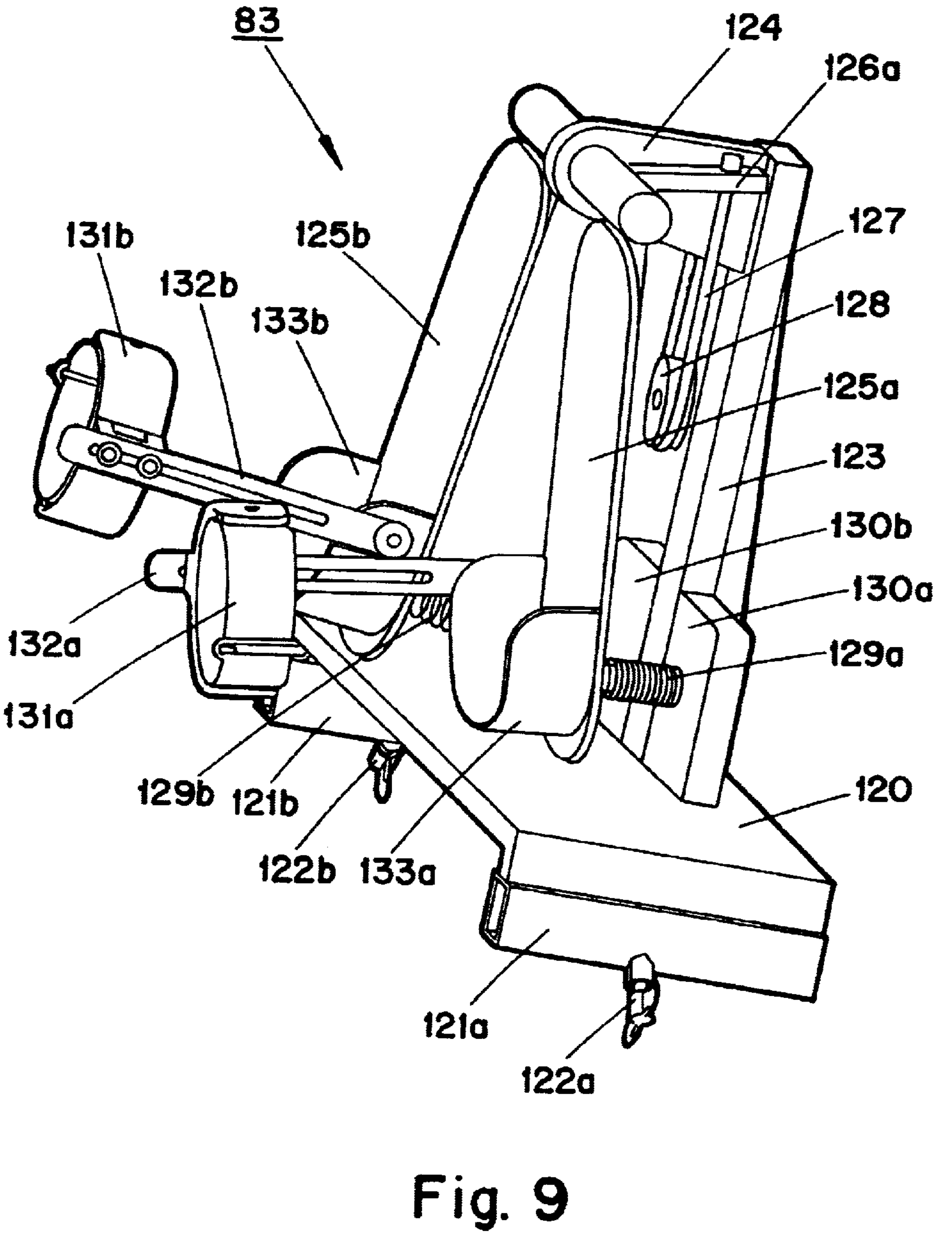
FIG. 9 shows the foot mechanism of FIG. 7, in a perspective diagram.

FIG. 9 shows the foot mechanism 83 of FIG. 7 in a perspective diagram. Respective rectangular tubes 121*a* and 121*b* are securely connected to the underside of a plate 120. These serve as guides for the foot mechanism on the rails fastened to the leg portion. The foot mechanism can be screwed fast with fastening screws 122*a* and 122*b* at the correct position in therapy. A support 123 is fastened to the plate 120 and a second support 124 is mounted on its upper end. A respective footplate 125*a* or 125*b* is situated on either side of the support 124, and is capable of rotation around a bearing at the point of attachment to the support 124. A respective footplate 125*a* or 125*b* is situated on either side of the support 124 and is capable of rotation around a bearing at the point of attachment to the support 124. Respective levers 126*a*, 126*b* (not shown) are fastened to the footplates, and are connected together by means of a steel cable 127. This steel cable 127 runs over a roller 128 and serves as a reciprocating mechanism. When a footplate is pressed downward, the other moves upward. Respective springs 129*a* or 129*b* are situated under the footplates 125*a* and 125*b*, and are tensioned on respective plates 130*a* or 130*b*. If one of the footplates pressed downward (extension) by the patient's leg, the other leg is automatically bent by the reciprocating mechanism. In addition, a weight force (afferent input) arises on the sole of the patient's foot due to the spring 129 when the leg is extended.

The patient's leg can be secured with respective cuffs 131*a* or 131*b*, which are connected to the footplates 125*a*, 125*b* by means of respective connecting cables 132*a* or 132*b*. It is thus laterally stabilized so as not to tilt to the side in the bent state. A heel holder 133*a* or 133*b* protects the patient's foot from slipping down from the footplate 125*a* or 125*b*.

With the active standing table according to the invention, it is possible to control the course of movement of all joint planes (hip, knee, foot) of the patient's lower extremities in a physiological pattern (kinematic and kinetic) as similar as possible to that of walking. The most important movement quantities for a successful locomotion therapy (excitation of locomotive activity) are the hip joint extension and the weight loading of the sole of the foot during the extension phase of the leg. Both parameters can be individually matched to the patient's needs with the active standing table described here.

In addition the active standing table can be adapted to the individual differences of patients' measurements.

Results can be attained with locomotion therapy on the active standing table, because training can be begun very early, i.e., even when the patient should not be raised upright.

What is claimed is:

1. Apparatus for locomotion therapy for the rehabilitation of paraparetic and hemiparetic patients, comprising a standing table adjustable in height and inclination, a fastening belt with holding devices on the standing table for the patient, a drive mechanism for the leg movement of the patient, consisting of a knee mechanism and a foot mechanism, wherein the standing table has a head portion displaceable with respect to a leg portion about a pivot point, whereby the pivot point provides an adjustable hip extension angle for which an adjusting mechanism is provided; and the knee portion and foot portion are displaceably arranged on rails on the leg mechanism; and the mechanism foot mechanism serves to establish force on the sole of the foot during knee extension; and a control unit is provided for controlling movement of the apparatus.

2. Apparatus according to claim 1, wherein two linear drives are provided for a knee mechanism, to extend or flex the patient's legs.

3. Apparatus according to claim 1, wherein an eccentric drive is provided for the knee mechanism, and alternately extends one of the legs; and the legs are bent again by the cushions of the knee mechanism and a reciprocating mechanism situated on the foot mechanism.

4. Apparatus according to claim 1, wherein the foot mechanism can generate a weight force in the extended phase of the leg, two springs being arranged for the production of this weight force.

5. Apparatus according to claim 1, wherein the hip extension angle has a value of 0–20°, and preferably 12°.

6. Apparatus according to claim 1, wherein the knee mechanism and the foot mechanism are displaceable on two rails and the active standing table can so be matched to the patient's measurements, all positions having markings by means of which desired settings are reproduced.

7. Apparatus according to claim 3, wherein a snap coupling is installed on the knee mechanism and unlatches under a tension of 150–200 N, preferably 180 N, and thus protects the knee from overloading.

8. Process for the operation of an apparatus according to claim 1, wherein the knee mechanism and the foot mechanism are displaced on the standing table in order thereby to match the drive to the patient's leg length; and an extension of the hip joint is predetermined by means of the hip extension angle and the angle of inclination; and a movement of the patient's legs is effected with the knee mechanism situated on the knee portion and with the foot mechanism, generating an afferent input or sensory information to the spinal cord like that arising in normal walking; and a weight force is produced on the sole of the foot during the knee extension; and the drives for the movements are controlled by the control unit which predetermines a pattern of movement similar to that of physiological walking.

9. Process according to claim 8, wherein the amount of movement is altered by the control unit or by the position of a pin on an eccentric drive.

10. Process according to claim 8, wherein the speed of the leg movement is varied.

11. Process according to claim 8, wherein the weight force acting on the sole of the foot in the extended phase of the leg movement is set by displaceable springs.

12. Process according to claim 8, wherein the positions of the knee mechanism and foot mechanism are read off, established, and reconstructed on markings.

* * * * *